United States Patent
Owoc

(10) Patent No.: US 8,445,466 B2
(45) Date of Patent: May 21, 2013

(54) STABLE AQUEOUS COMPOSITIONS COMPRISING AMIDE-PROTECTED BIOACTIVE CREATINE SPECIES AND USES THEREOF

(76) Inventor: John H. Owoc, Weston, FL (US)

( * ) Notice: Subject to any disclaimer, the term of this patent is extended or adjusted under 35 U.S.C. 154(b) by 339 days.

(21) Appl. No.: 12/756,686

(22) Filed: Apr. 8, 2010

(65) Prior Publication Data

US 2011/0251280 A1    Oct. 13, 2011

(51) Int. Cl.
*A01N 33/26* (2006.01)
(52) U.S. Cl.
USPC .......................................... 514/150; 514/151
(58) Field of Classification Search
USPC ................................................ 514/150, 151
See application file for complete search history.

(56) References Cited

U.S. PATENT DOCUMENTS

| | | | | |
|---|---|---|---|---|
| 7,709,529 B2 * | 5/2010 | Klimberg et al. | ............. | 514/561 |
| 2007/0248737 A1 * | 10/2007 | Kulkarni et al. | ............. | 426/597 |

FOREIGN PATENT DOCUMENTS

| | | |
|---|---|---|
| CN | 101012240 | 8/2007 |
| EP | 2 269 980 | 1/2011 |
| WO | WO 2006/034586 | 4/2006 |
| WO | WO 2009/126174 | 10/2009 |
| WO | WO 2010/074591 | 7/2010 |

OTHER PUBLICATIONS

Buford et al., "International Society of Sports Nutrition position stand: creatine supplementation and exercise", *Journal of the International Society of Sports Nutrition*, Aug. 2007, vol. 4, No. 6, 8 pages.
Evangeliou et al., "Clinical Applications of creatine supplementation on paediatrics", *Current Pharmaceutical Biotechnology*, 2009, vol. 10, No. 7, pp. 683-690.
Harris et al., "Absorption of creatine supplied as a drink, in meat or in solid form", *Journal of Sports Sciences*, 2002, vol. 20, No. 2, pp. 147-151.
Hass et al., "Resistance training with creatine monohydrate improves upper-body strength in patients with Parkinson Disease: a randomized trial", *Neurorehabilitation and Neural Repair*, 2007, vol. 21, No. 2, pp. 107-115.
Juhász et al., "Creatine supplementation improves the anaerobic performance of elite junior fin swimmers", *Acta Physiologica Hungarica*, 2009, vol. 96, No. 3, abstract.
Kreider et al., "Long-term creatine supplementation does not significantly affect clinical markers of health in athletes", *Molecular and Cellular Biochemistry*, 2003, vol. 244, pp. 95-104.
Ling et al., "Cognitive effects of creatine ethyl ester supplementation", *Behavioural Pharmacology*, 2009, vol. 20, No. 8, pp. 673-679.
Poortmans et al., "Adverse effects of creatine supplementation: fact or fiction?", *Sports Medicine*, Sep. 2000, vol. 30, No. 3, pp. 155-170.
Powers et al., "Creatine supplementation increases total body water without altering fluid distribution", *Journal of Athletic Training*, 2003, vol. 38, No. 1, pp. 44-50.
Rawson et al., "Effects of creatine supplementation and resistance training on muscle strength and weightlifting performance", *Journal of Strength and Conditioning Research*, 2003, vol. 17, No. 4, pp. 822-831.
Spillane et al., "The effects of creatine ethyl ester supplementation combined with heavy resistance training on body composition, muscle performance, and serum and muscle creatine levels", *Journal of the International Society of Sports Nutrition*, Feb. 2009, vol. 6, No. 6, 14 pages.
Stout et al., "Effects of resistance exercise and creatine supplementation on *Myasthenia gravis*: a case study", *Medicine & Science in Sports & Exercise*, 2001, vol. 33, No. 6, pp. 869-872.
Vorgerd et al., "Creatine therapy in Myophosphorylase deficiency (McArdle disease)", *Archives of Neurology*, Jul. 2000, vol. 57, No. 7, pp. 956-963.
Wyss et al., "Health implications of creatine: can oral creatine supplementation protect against neurological and atherosclerotic disease?", *Neuroscience*, 2002, vol. 112, No. 2, pp. 243-260.

* cited by examiner

*Primary Examiner* — Renee Claytor
(74) *Attorney, Agent, or Firm* — Saliwanchik, Lloyd & Eisenschenk

(57) ABSTRACT

The present invention provides amide-protected creatine molecules and compositions, containing one or more bioactive forms of creatine in aqueous compositions, wherein bioactive forms of creatine do not appreciably degrade into creatinine. Also provided are various beneficial effects of administering aqueous compositions having at least one amide-protected creatine molecule.

12 Claims, No Drawings

STABLE AQUEOUS COMPOSITIONS COMPRISING AMIDE-PROTECTED BIOACTIVE CREATINE SPECIES AND USES THEREOF

TECHNICAL FIELD

This invention relates generally to stable aqueous solutions of creatine, methods for their preparation and methods of use.

BACKGROUND OF THE INVENTION

Many nutritional supplements are available at various retail outlets, in many forms, including tablets, pills, powders, and liquids intended for human consumption.

One nutritional supplement that has become popular is creatine, whose IUPAC name is 2-(carbamimidoyl-methylamino) acetic acid (CAS No. 57-00-1). Creatine occurs naturally in muscle and is believed to be an essential component in energy-producing metabolism and normal muscle function and growth. It is also believed by many to be useful to bodybuilders for increasing muscle mass, i.e., muscle-building.

Creatine supplementation offers a variety of health benefits. Studies have shown that creatine enhances athletic performance in the strength-power sports, promotes gains in lean body mass and muscle fiber hypertrophy (growth), improves neuromuscular function, especially in patients with metabolic diseases and decreased muscular fitness, and improves neural function and cognitive abilities. In addition, no adverse health effect has been observed in both short- or long-term creatine supplementations. In a thorough scientific review published in the Journal of Strength and Conditioning, scientists summarized 22 published studies, and concluded that the average increase in muscle strength following creatine supplementation during resistance training was 8% greater than the average increase in muscle strength following placebo ingestion during resistance training (20% vs. 12%). Also, the average increase in weightlifting performance (maximal repetitions at a given percent of maximal strength) following creatine supplementation during resistance training was 14% greater than the average increase in weightlifting performance following placebo ingestion during resistance training (26% vs. 12%). In addition, creatine supplementation improves the bench press 1-Rep Max (RM) performance of 3% to 45%, and the weightlifting performance in the bench press of 16% to 43%.(1)

In addition, scientists tested the hypothesis whether oral creatine supplementation 5 grams daily for six weeks would enhance intelligence test scores and working memory performance in 45 young adult, vegetarian subjects in a double-blind, placebo-controlled, cross-over design. The results showed that creatine supplementation significantly improves both working memory (backward digit span) and intelligence (Raven's Advanced Progressive Matrices).(2)

Furthermore, creatine supplementation has neuroprotective effects, useful for preventing and treating neurological diseases such as Huntington's disease, Parkinson's disease, or amyotrophic lateral sclerosis.(3) One investigation found that 5 grams of creatine supplementation daily, coupled with resistance training (3× per week for 15 weeks), improved physical function in a 26-year-old man with myasthenia gravis. This individual had a 7% increase in body weight, 4% increase in fat free mass, and improved peak strength up to 37%. (4) Another investigation found that creatine supplementation improves skeletal muscle function in patients with McArdle disease.(5)

In addition, creatine supplementation significantly enhances muscular fitness of patients with Parkinson disease (PD), who exhibit decreased muscular fitness, including decreased muscle mass, muscle strength, and increased fatigability. Twenty patients with idiopathic PD were randomized to receive creatine monohydrate supplementation during resistance training (CRE) or placebo (lactose monohydrate) during resistance training (PLA), using a double-blind procedure. Both the creatine and placebo supplementation consisted of 20 g/d for the first 5 days and 5 g/d thereafter. Both groups participated in progressive resistance training (24 sessions, 2 times per week, 1 set of 8-12 repetitions, 9 exercises). Creatine supplementation significantly improved chest press strength and biceps curl strength.(7)

There are also data concerning the short and long-term therapeutic benefits of creatine supplementation in children and adults with gyrate atrophy (a result of the inborn error of metabolism with ornithine delta-aminotransferase activity), muscular dystrophy (facioscapulohumeral dystrophy, Becker dystrophy, Duchenne dystrophy and sarcoglycan deficient limb girdle muscular dystrophy), McArdle's disease, Huntington's disease and mitochondria-related diseases. Hypoxia and energy related brain pathologies (brain trauma, cerebral ischemia, prematurity) could benefit from Cr supplementation.(12) Creatine supplementation has also been shown to lead to an improvement in various cognitive tasks.(13)

More beneficially, there is no scientific evidence that the short- or long-term use of creatine monohydrate has any detrimental effects on otherwise healthy individuals. In fact, five days of creatine supplementation enhances the dynamic strength and may increase anaerobic metabolism in the lower extremity muscles, and improves performance in consecutive maximal swims in highly trained adolescent (mean age 16) fin swimmers.(11)

No adverse effects on renal function has been observed in short term (5 days), medium term (9 weeks) and long term (up to 5 years) oral creatine supplementation in small cohorts of athletes.(8) Another investigation examined over a 21-month period, 98 Division IA college football players who consumed in an open label manner creatine or non-creatine containing supplements following training sessions. Subjects who ingested creatine were administered 15.75 g/day of creatine monohydrate for five days and an average of 5 g/day thereafter in 5-10 g/day doses. No adverse effect has been observed in long-term creatine supplementation (up to 21-months).(9)

According to the position stand published by the International Society of Sports Nutrition(10), creatine is the most effective ergogenic nutritional supplement currently available to athletes in terms of increasing high-intensity exercise capacity and lean body mass during training. Also, supplementation is not only safe, but possibly beneficial in regard to preventing injury and/or management of select medical conditions when taken within recommended guidelines.

Despite its significant health benefits, creatine supplementation can only be offered in powder, pill or capsule form. Currently, no aqueous-based formulation containing appreciable amounts of creatine, intended for oral human consumption, is available in the marketplace. This is because creatine is unstable in aqueous systems, in which it rearranges to creatinine.

The rate of creatine degradation in aqueous systems can be determined based on serum creatinine concentration. Creatine is non-enzymatically converted into creatinine at approximately 1.7% daily in a typical 70 kg individual. The skeletal muscle represents the primary site of creatinine production.

Creatine is also degraded in the GI tract into creatinine at an estimated rate of 0.1 g of a 5 g dose per hour.

Creatinine has no nutritional benefits and does not enhance muscle fitness. Moreover, abnormal serum creatinine levels may be correlated with serious disease or renal dysfunction. For example, blood creatinine levels are used as a measure of renal function, and abnormally high levels indicate possible renal dysfunction.

Conditions leading to high blood creatinine levels further include blockage of the urinary tract (such as by a kidney stone), heart failure, dehydration, excessive blood loss that causes shock, gout, or muscle conditions (such as rhabdomyolysis, gigantism, acromegaly, myasthenia gravis, muscular dystrophy, and polymyositis). Usually a high blood creatinine level means that the creatinine clearance value is lower than normal.

There is a critical need in the art for a creatine composition that is stable in aqueous systems.

BRIEF SUMMARY

The subject invention provides stable aqueous compositions of at least one amide-protected, biologically-active form of creatine (creatyl-amide) molecule, wherein the carboxylic acid group of creatine is linked to, for example, an amino group of an amine, an amino acid or a peptide, thereby forming an amide bond. In a preferred embodiment, the compositions of the subject invention comprise:

a) at least one creatyl-amide species, wherein the carboxylic acid group of creatine is linked to an amino group of an amine, an amino acid or a peptide, thereby forming an amide bond; and b) water.

In preferred embodiments, the stable aqueous compositions have a pH of about 1.5 to about 6.5, and contain creatyl-L-glutamine, creatyl-L-leucine, creatyl-L-carnosine, creatyl-1-methylhistidine, and/or creatyl-beta-alanyl-1-methylhistidine.

Advantageously, these compositions are stable across a wide range of pHs and temperatures. These formulations are stable at temperatures between 4° C. (or less) and 40° C. (or higher). Advantageously, across this wide range of conditions, the concentration of bioactive species in these compositions does not decrease appreciably over periods of 40 or even 60 days or more.

The compositions of the subject invention may further comprise one or more additional materials selected from, for example, flavoring agents, colorants, viscosity modifiers, preservatives, fragrances, amino acids and their salts, vitamins, minerals, essential fatty acids, enzymes, co-enzymes, mono-glycerides, di-glycerides, tri-glyceride ester oils emulsifiers, hydrolyzed proteins, whey protein, stabilizers, flow modifiers, viscosity improvers, chelating agents, anti-oxidants, anti-microbials, benzoates, alcohols, esters of para-hydroxybenzoic acid, propionates, preservatives and surfactants.

The subject invention further provides methods for preparing and using these compositions. In preferred embodiments, the amide-protected creatine compositions can be formulated into nutritional supplements, aqueous and emulsion injectable formulations, aqueous clear gel systems, creams and lotions, active-in-adhesive transdermal systems, and aqueous liquid-reservoir transdermal patches.

The compositions of the subject invention can provide any one or more of a wide range of physiological benefits including, for example, regeneration of ADP to ATP in muscle tissue, increasing the serum concentration of creatine, increasing muscle fiber size/cross-sectional area and lean body mass, activating satellite cells, enhancing memory and cognitive function, enhancing the functional capacity of a mammal having a neuromuscular disease, increasing muscular strength, endurance and/or power, enhancing cognitive function in infants with inborn errors of creatine metabolism, and/or alleviating the deleterious effects of sleep deprivation.

DETAILED DESCRIPTION

The present invention provides amide-protected, biologically-active creatine (creatyl-amide) molecules and aqueous compositions containing these amide-protected creatine molecules. In preferred embodiments, the carboxylic acid group of creatine is linked to an amino group of an amine, an amino acid or a peptide, thereby forming an amide bond.

Advantageously, these amide-protected creatine molecules are stable in aqueous systems and suitable for administration to mammalian subjects. In a preferred embodiment, the stable aqueous compositions have a pH of about 1.5 to about 6.5, and the amide-protected creatine molecules are creatyl-L-glutamine, creatyl-L-leucine, creatyl-L-carnosine, creatyl-1-methylhistidine, and/or creatyl-beta-alanyl-1-methylhistidine.

Further provided are methods of making and using these molecules and compositions.

Creatyl-Amide Compounds

In a first aspect, this invention provides amide-protected creatine molecules, wherein creatine is stabilized by protecting its carboxylic acid group. Creatine, as used herein, encompasses all biologically-active forms of creatine, and salts, derivatives and analogs thereof, including but not limited to, creatine monohydrate, disodium creatine phosphate tetrahydrate, and creatine hydrochloride.

In one embodiment, the general chemical formula of amide-protected creatine molecules of the subject invention is illustrated below, wherein the carboxylic acid group of creatine has been reacted with a molecule (R—NH) that contributes an amine group thereby forming the amide having the following formula:

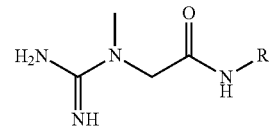

Preferably, the R—NH molecule that contributes the amine group is an amino acid or peptide.

The amide-protected creatine molecules, such as creatyl-L-glutamine and creatyl-L-leucine, are substantially stable in aqueous media. The covalent amide bond formed between creatine and the protecting group exhibits unexpectedly improved hydrolysis-stability.

Specifically, water alone is not sufficient to hydrolyze the amides. Rather, in addition to acid or basic conditions, the hydrolysis of the amide bond requires the presence of catalysts and/or prolonged heating.

In one embodiment, the carboxylic acid group of creatine is covalently linked to an amino acid molecule. In a specific embodiment, the carboxylic acid group of creatine is covalently linked to the amino group of glutamine and/or leucine.

In a specific embodiment, the creatyl-amide molecule is creatyl-L-glutamine:

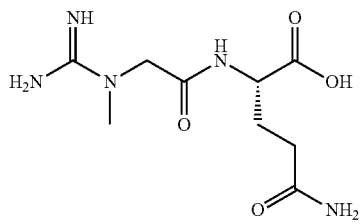

(I) Creatyl-L-Glutamine; IUPAC Name: 2s)-2-(2-carbamimidoyl-methyl-amino)acetamido)-4-aminocarbonyl-butanoic acid Formula: $C_9H_{17}N_5O_4$
MW=259.26

In another specific embodiment, the creatyl-amide molecule is creatyl-L-leucine:

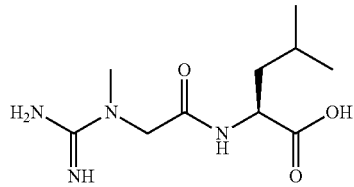

(II) Creatyl-L-Leucine; (2s)-2-(2-(carbamimidoyl-methyl-amino)acetamido)-4-methylpetanoic acid Formula: $C_{10}H_{20}N_4O_3$
MW=244.29

In certain embodiments, creatine is protected with an amino acid selected from glutamine, leucine, arginine, histidine, isoleucine, lysine, methionine, phenylalanine, threonine, tryptophan, tyrosine, valine, alanine, asparagine, aspartate, cysteine, glutamate, glycine, proline, serine, and glutamic acid.

Preferably, creatine is protected with an L-amino acid selected from L-glutamine, L-leucine, L-arginine, L-histidine, L-isoleucine, L-lysine, L-methionine, L-phenylalanine, L-threonine, L-tryptophan, L-tyrosine, L-valine, L-alanine, L-asparagine, L-aspartate, L-cysteine, L-glutamate, glycine, L-proline, L-serine, and L-glutamic acid.

In another embodiment, creatine is stabilized by protecting the carboxylic group with a peptide. Useful peptides include, for example, di-peptides, tri-peptides, tetra-peptides, penta-peptides, and long-chain oligo-peptides. In certain embodiments, peptides useful for protecting creatine are composed of amino acids selected from the group consisting of glutamine, leucine, arginine, histidine, isoleucine, lysine, methionine, phenylalanine, threonine, tryptophan, tyrosine, valine, alanine, asparagine, aspartate, cysteine, glutamate, glycine, proline, serine, and glutamic acid. These peptides can be used to bond to creatine's carboxylic group, thereby forming an amide bond to stabilize creatine.

Preferably, the carboxylic acid group of creatine is protected by a natural amino acid molecule or a peptide composed of natural amino acids. In a further embodiment, creatine is stabilized by protecting the carboxylic group with a derivative of a natural amino acid or a peptide composed of natural amino acids, where any functional group of a side chain of the amino acid may be modified with one or more of the following groups, including but not limited to, alkyl, acyl, carboxyl, halo, carboxyl, carboalkoxy, carboxamide, haloalkyl, amino, alkylamino, hydroxy, hydroxyalkyl, and alkoxy of any length and structure.

In a preferred embodiment, the carboxylic group of creatine is protected by an amino acid derivative with similar structure-function to glutamine or leucine.

In certain embodiments, creatine is stabilized by protecting the carboxylic group with an amine, an amino acid, or a peptide, including but not limited to, natural amino acids; non-natural amino acids, such as for example, sarcosine, β-alanine, citrulline, ornithine, and prolinamide; hydroxylated amino acids, such as for example, 5-hydroxy lysine; dipeptides, such as for example, alanyl-L-glutamine; tripeptides; oligopeptides; and nutrient chemicals, such as for example, taurine, geranamine.

In a specific embodiment, creatine is stabilized by protecting the carboxylic group with carnosine (beta-alanyl-L-histidine), methylhistidine, or beta-alanyl methylhistidine.

Exemplified embodiments of creaty-amide molecules are shown below.

Creatyl-L-Essential Amino Acid Peptides

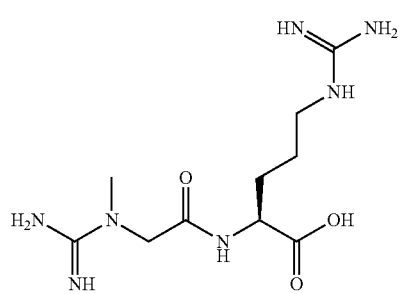

Creatyl-L-Arginine

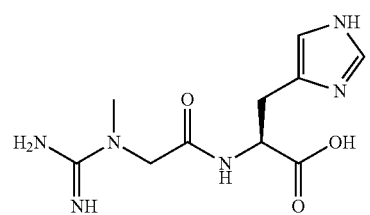

Creatyl-L-Histidine

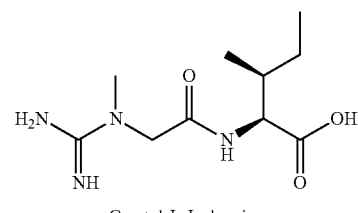

Creatyl-L-Isoleucine

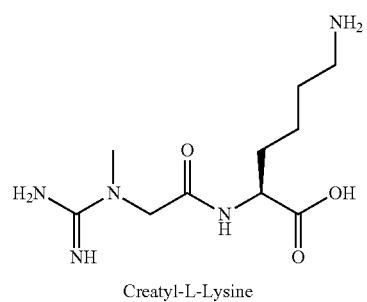
Creatyl-L-Lysine (VI)
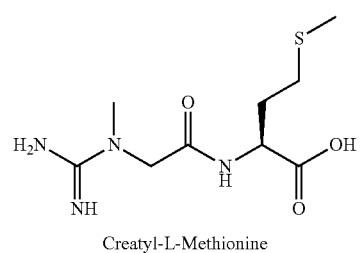
Creatyl-L-Methionine (VII)
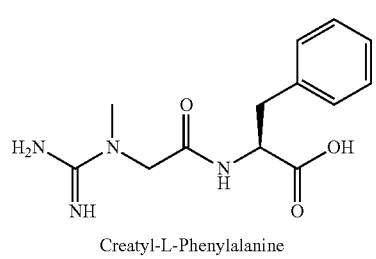
Creatyl-L-Phenylalanine (VIII)
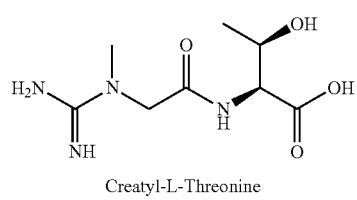
Creatyl-L-Threonine (IX)
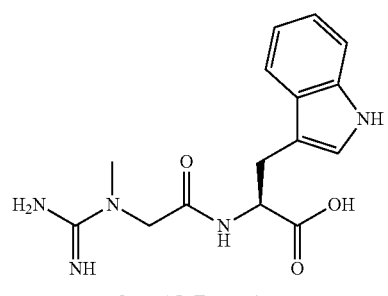
Creatyl-L-Tryptophan
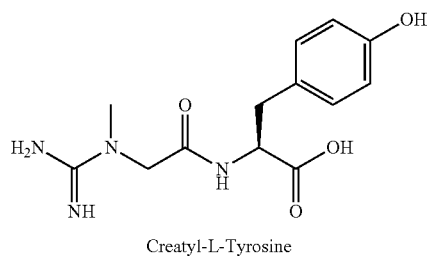
Creatyl-L-Tyrosine (XI)
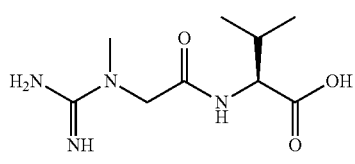
Creatyl-L-Valine (XII)
Creatyl-L-Unessential Amino Acid Peptides
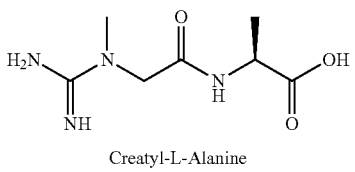
Creatyl-L-Alanine (XIII)
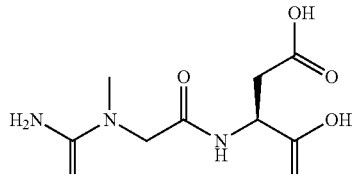
Creatyl-L-Asparagine (XIV)
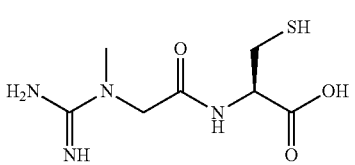
Creatyl-L-Aspartate (XV)
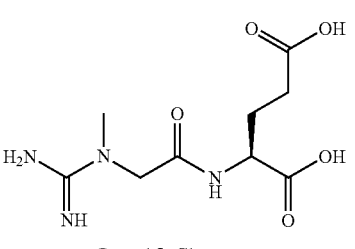
Creatyl-L-Cysteine (XVI)
Creatyl-L-Glutamate (XVII)
Creatyl Glycine (XIII)

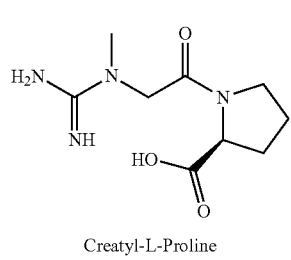

Creatyl-L-Proline (XIX)

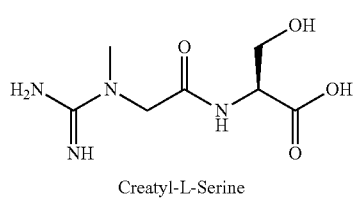

Creatyl-L-Serine (XX)

The compounds of formulae (I) through (XX) above are all creatyl-amino acid species of the present invention.

Furthermore, this invention provides methods for synthesis of amide-protected creatine molecules.

To illustrate, creatyl-L-glutamine can be synthesized as follows. First, L-glutamine as the starting material is reacted with 2-chloroacetyl chloride to obtain N-chloroacetyl-L-Glutamine. This intermediate is converted to sarcosyl-L-glutamine in aqueous methylamine solution. Sarcosyl-L-glutamine is further treated to obtain creatyl-L-glutamine. In this way, a dipeptide creatyl-L-glutamine is obtained from glutamine.

The synthesis of creatyl-amide species of the present invention, such as for example, creatyl-L-leucine, creatyl-L-carnosine, creatyl-1-methylhistidine and creatyl-beta-alanyl-1-methylhistidine, can be achieved in a similar manner, except that different amino acid acids or peptides, such as L-leucine, L-carnosine, 1-methylhistidine and beta-alanyl-1-methylhistidine, are used as the starting materials. Advantageously, amide-protection of creatine carboxylic group prevents the carboxylic group and guanidine group of creatine to react and dehydrate to produce creatinine.

A further advantage of the present invention is that the amide bond of creatyl-amide species (e.g., creatyl-L-glutamine, creatyl-L-leucine, creatyl-L-carnosine, creatyl-1-methylhistidine and creatyl-beta-alanyl-1-methylhistidine) can be hydrolyzed in the digestive system by enzymes to release pure creatine and useful amino acids, such as glutamine, leucine, carnosine, 1-methylhistidine and beta-alanyl-1-methylhistidine. Moreover, certain amino acids, such as leucine, have insulinogenic effects, thereby increasing insulin levels to facilitate the shuttling of amino acids into muscle.

Amide-Protected Creatine Compositions

The subject invention provides stable aqueous compositions of at least one biologically-active form of amide-protected creatine molecule. In one embodiment, the composition of the present invention comprises:

a) at least one biologically-active form of amide-protected creatine, wherein the carboxylic acid group of creatine is linked to an amino group of an amine, an amino acid or a peptide, thereby forming an amide bond; and b) water.

In one embodiment, the amide-protected creatine is creatyl-L-glutamine or creatyl-L-leucine. In other embodiments, the amide-protected creatine molecule is creatyl-L-carnosine, creatyl-1-methylhistidine, or creatyl-beta-alanyl-1-methylhistidine. Optionally, the composition is buffered at a pH of about 1.5 to about 6.5.

The subject invention further provides methods for preparing and using these compositions.

The amide-protected creatine compositions can be formulated into nutritional supplements, aqueous and emulsion injectable formulations, aqueous clear gel systems, creams and lotions, active-in-adhesive transdermal systems, and aqueous liquid-reservoir transdermal patches.

Specifically exemplified herein are compositions for oral use. The subject invention further provides compositions for injection as well as for topical administration.

In a specific embodiment, the subject invention provides aqueous compositions suitable for oral administration to mammals including, without limitation, humans.

A composition as provided herein may be administered chronically. As used herein, "chronically" means repeated ingestion over a period of several days, several weeks, even several months, or longer. Acute (non-chronic) administration may also be utilized.

In one embodiment, the subject invention provides aqueous compositions having a pH in the range of about 1.5 to about 6.5. The pH can be obtained by using appropriate amounts of strong or weak acids or bases including, without limitation, aqueous mineral acids including HCl, $H_3PO_4$, and bases including sodium hydroxide, ethanolamines, etc. Preferably, the pH is from about 3.0 to about 6.5.

To prepare a composition according to one embodiment of this invention, a desired amount of creatyl-L-glutamine can be added to a selected volume of water, and sufficient stirring is affected to cause dissolution of the creatyl-L-glutamine to create an aqueous composition.

The total concentration of creatyl-L-glutamine species in an aqueous solution provided hereby may be any amount between about 0.1% and about 25% by weight based on the total weight of the aqueous solution, including all percentages and ranges of percentages therebetween.

Alternatively, creatyl-L-glutamine (or any one or more creatyl-L-glutamine species) may be added to a natural beverage in any amount provided that an aqueous solution or suspension results.

Similar embodiments of compositions may be obtained with creatyl-L-leucine, creatyl-L-carnosine, creatyl-1-methylhistidine, and creatyl-beta-alanyl-1-methylhistidine.

According to additional embodiments, one or more ions selected from: sodium, potassium, zinc, calcium, and magnesium (collectively, "metal cations") are additionally present in the aqueous solution comprising creatyl-L-glutamine. These metal cations may be provided by adding a soluble salt or any other material containing any one or more of the metal cations to any aqueous solution containing creatyl-L-glutamine, or may be added to water or any aqueous solution prior to addition of one or more creatyl-L-glutamine thereto.

The total concentration of these one or more metal cations may be any amount between about 0.001% and about 10% by weight based on the total weight of the aqueous solution, including all percentages and ranges of percentages therebetween. Such metal ions may derive from a salt or compound containing a creatyl-L-glutamine, or may derive from other ingredients added to the composition. Such other ingredients include, without limitation, alkali metal halides, alkaline earth metal halides, alkali metal carboxylates, alkaline earth metal carboxylates, and any other materials known to those skilled in the nutritional arts, which comprise such metal cations as part of their molecular structure or formula, which are not deleterious to mammalian organisms at the concentration level at which they are present, which is generally known in the art.

Similar embodiments of compositions may be obtained with creatyl-L-leucine, creatyl-L-carnosine, creatyl-1-methylhistidine, and creatyl-beta-alanyl-1-methylhistidine.

A composition according to this invention may also include other ingredients such as, for example, flavoring agents, colorants, viscosity modifiers, preservatives, chelating agents, antioxidants, surface modifiers and other nutritional adjuvant materials. Other materials include any substance that is generally recognized as promoting the health or function of a mammalian organism, including humans, or benefiting a composition useful thereof in terms of its efficacy, appearance, stability, consistency, aroma, or viscosity. Such substances include, for example, other amino acids and their salts, vitamins, minerals, fatty acids, enzymes, monoglycerides, di-glycerides, tri-glyceride ester oils (including, for example, vegetable oils and animal fats) emulsifiers, hydrolyzed proteins, whey protein, stabilizers, flow modifiers, viscosity improvers, chelating agents, enzymes, and surfactants (whether anionic, cationic or nonionic). The total amount of these materials in a composition can be any amount between about 0.01% and about 50% by weight based on the total weight of said composition, including all percentages and ranges of percentages therebetween.

A composition according to this invention may also comprise one or more natural or synthetic beverages. For example, a natural beverage may contain the pulp, juice or any other constituent of a naturally-occurring fruit, vegetable, or animal product whether from the wild, cultured, cultivated on a farm or otherwise domesticated.

Natural beverages include, without limitation, materials such as milk products, soy products, ice cream, yogurt, citrus fruit juices, non-citrus fruit juices, and vegetable juices, or components of any of the foregoing, wherein said natural beverages are present in any effective amount to impart flavor to the compositions, which may be any amount between about 0.1% and about 99% by weight based on the total weight of said composition, including all percentages and ranges of percentages there between.

In general, a composition according to this invention may be provided by combining and mixing the ingredients selected, including creatyl-L-glutamine, creatyl-L-leucine, creatyl-L-carnosine, creatyl-1-methylhistidine or creatyl-beta-alanyl-1-methylhistidine, and any desired quantity of any one or more other ingredients specified herein. One advantage of compositions according to this invention is that they may be packaged at pH levels as low as about pH 3, in the cold or at about room temperature or only slightly elevated temperatures, as opposed to many prior art compositions which typically require hot packaging methods that utilize specialized and expensive equipment and packaging materials.

Thus, it is evident that a composition according to this invention may be made quite palatable to a mammalian subject, including a human. Serving sizes may be any serving size in the range of about 1 milligram to about 50 grams, in an aqueous solution that is from about 20 ml to about 2500 ml in volume. The amount of creatyl-amide species (e.g. creatyl-L-glutamine, creatyl-L-leucine, creatyl-L-carnosine, creatyl-1-methylhistidine and creatyl-beta-alanyl-1-methylhistidine) in an aqueous composition according to this invention is limited only by the solubility limit of the creatyl-amide species, which may exceed 50 grams per liter and concentrations at or near the solubility limit are herein provided by contacting excess amounts of the creatyl-amide species (e.g. creatyl-L-glutamine, creatyl-L-leucine, creatyl-L-carnosine, creatyl-1-methylhistidine and creatyl-beta-alanyl-1-methylhistidine) with water or an aqueous solution to provide a solution saturated with creatyl-amide species (e.g. creatyl-L-glutamine, creatyl-L-leucine, creatyl-L-carnosine, creatyl-1-methylhistidine and creatyl-beta-alanyl-1-methylhistidine). Such saturated solutions can provide a concentrate from which other creatyl-amide-containing compositions may be conveniently provided.

The compositions of the subject invention can be formulated for a variety of modes of administration. These formulations include, but are not limited to, compositions for oral administration, aqueous injectable formulations, injectable emulsion compositions, gel formulations, cream formulations, transdermal systems, transdermal patch systems, liquid buccal sublingual solutions, oral solid compositions, and oral liquid composition with protein.

Physiological and Health Benefits

The compositions of the subject invention can be used in a variety of advantageous methods. For example, these compositions can be used in methods which cause regeneration of ADP to ATP in muscle tissue, cause an increase in the serum concentration of creatine, increase muscle fiber size/cross-sectional area and lean body mass, activate satellite cells, enhance memory and cognitive function, enhance the functional capacity of a mammal having a neuromuscular disease, increase muscular strength, endurance and/or power, enhance cognitive function in infants with inborn errors of creatine metabolism, or alleviate the deleterious effects of sleep deprivation.

The amide-protected creatine molecules and compositions of the subject invention offer a variety of physiological and health benefits including, for example, regeneration of ADP to ATP in the muscle tissue of the mammal, increasing serum concentration of creatine, increasing muscle fiber size/cross-sectional area and lean body mass, activating satellite cells, enhancing memory and cognitive function in the mammal, enhancing the functional capacity of a subject having a neuromuscular disease such as Huntington's disease, Parkinson's disease, or amyotrophic lateral sclerosis, increasing muscular strength, endurance and/or power, enhancing function in infants with inborn errors of creatine metabolism, and/or alleviating the deleterious effects of sleep deprivation.

In addition, creatine supplementation has beneficial effects on a subject with gyrate atrophy (a result of the inborn error of metabolism with ornithine delta-aminotransferase activity), muscular dystrophy (facioscapulohumeral dystrophy, Becker dystrophy, Duchenne dystrophy and sarcoglycan deficient limb girdle muscular dystrophy), McArdle's disease, Huntington's disease and mitochondria-related diseases. Hypoxia and energy related brain pathologies (brain trauma, cerebral ischemia, prematurity) might also benefit from creatine supplementation.

Following are examples that illustrate procedures for practicing the invention. These examples should not be construed as limiting. All percentages are by weight and all solvent mixture proportions are by volume unless otherwise noted.

EXAMPLE 1

Liquid Ready-to-Drink Compositions

This Example illustrates an oral liquid composition (Ready-to-Drink), comprising creatyl-amide species, such as creatyl-L-glutamine or creatyl-L-leucine. The composition has a pH of about 3 to 6.5, and is substantially stable at room temperature for normal warehouse storage conditions, stable at 104° F. (40° C.) for shipping in hot weather trucks and/or overseas containers, and stable at 39° F. (4° C.) in coolers so that it can be stored under refrigeration conditions.

Preferably, the composition comprises a suitable aqueous solvent or vehicle, a non-aqueous vehicle, a preservative, a physical stabilizing ingredient, one or more surfactants, and/or one or more buffer salts that can render the composition pH stable. The composition may also contain nucleotides, oligonucleotides, the monophosphates, diphosphates, triphosphates and cyclic derivatives of these nucleotides, amino acids, vitamins and vitamin-like isoprenoids, peptides and one or more additional components selected from lipids, starches, carbohydrates, polyols, minerals, electrolytes, amino trace elements, colorings, flavors, artificial sweeteners, and anti-oxidants.

Illustrated below is a specifically exemplified embodiment of a ready-to-drink formulation of the subject invention.

Formulation I

| INGREDIENTS (Ready-to-Drink Formulation) | % w/w |
| --- | --- |
| Purified water | 97.1 |
| Creatyl-L-Glutamine or Creatyl-L-Leucine | 1.00 |
| Gamma Butyrobetaine | 0.0156 |
| Glycerin | 1.067 |
| Anserine | 0.052 |
| Caffeine | 0.06 |
| Magnesium Tanshinoate | 0.0000009 |
| L-Leucine | 0.104 |
| L-Isoleucine | 0.052 |
| L-Valine | 0.0208 |
| 1,3-di-n-propyl-7-propargylxanthine | 1E−10 |
| Geranamine | 0.0004 |
| Citric acid to pH 3.33 | 0.179 |
| Sodium benzoate | 0.052 |
| Potassium sorbate | 0.01 |
| Bis picolinate vanadium | 0.0000002 |
| Salt | 0.005 |
| Potassium phosphate dibasic | 0.0206 |
| Sodium Erythorbate | 0.000001 |
| Nisaplin | 0.000001 |
| Sucralose | 0.073 |
| Malic acid | 0.083 |
| Flavor Melon | 0.105 |

EXAMPLE 2

Compositions for Buccal Sublingual Administration

This Example illustrates an oral liquid composition for buccal sublingual administration, comprising creatyl-amide species, such as creatyl-L-glutamine or creatyl-L-leucine. The composition has a pH of about 3 to 6.5, and is substantially stable at room temperature for normal warehouse storage conditions, stable at 104° F. (40° C.) for shipping in hot weather trucks and/or overseas containers, and stable at 39° F. (4° C.) in coolers so that it can be stored under refrigeration conditions.

Preferably, the composition comprises a suitable aqueous solvent or vehicle, a non-aqueous vehicle, a preservative, a physical stabilizing ingredient, one or more surfactants, and/or one or more buffer salts that can render the composition pH stable. The composition may also contain nucleotides, oligonucleotides, the monophosphates, diphosphates, triphosphates and cyclic derivatives of these nucleotides, amino acids, vitamins and vitamin-like isoprenoids, peptides and one or more additional components selected from lipids, starches, carbohydrates, polyols, minerals, electrolytes, amino trace elements, colorings, flavors, artificial sweeteners, and anti-oxidants of the subject invention.

Illustrated below are specifically exemplified embodiments of liquid buccal sublingual solutions.

Formulation I

| INGREDIENTS | % w/w |
| --- | --- |
| Creatyl-L-Glutamine or Creatyl-L-Leucine | 2.10 |
| Peptides | 3.00 |
| AMP | 12.50 |
| UTP | 0.10 |
| Ubiquinone | 3.20 |
| Alcohol USP | 45.0 |
| Buffer Salt(s) | QS to adjust pH |
| Purified Water | QS to 100 |

Formulation II

| INGREDIENTS | % w/w |
| --- | --- |
| Creatyl-L-Glutamine or Creatyl-L-Leucine | 2.10 |
| Peptides | 3.00 |
| AMP | 12.50 |
| UTP | 0.10 |
| Ubiquinone | 3.20 |
| Ethoxydiglycol | 20.0 |
| Alcohol USP | 50.0 |
| Benzyl alcohol | 1.00 |
| Buffer Salt(s) | QS to adjust pH |
| Purified Water | QS to 100 |

Formulation III

| INGREDIENTS | % w/w |
| --- | --- |
| Creatyl-L-Glutamine or Creatyl-L-Leucine | 2.10 |
| Peptides | 3.00 |
| AMP | 12.50 |
| UTP | 0.10 |
| Ubiquinone | 3.20 |
| Propylene Glycol | 20.0 |
| Alcohol USP | 40.0 |
| Polysorbate 80 | 5.0 |
| Benzyl alcohol | 1.00 |
| Buffer Salt(s) | QS to adjust pH |
| Purified Water | QS to 100 |

EXAMPLE 3

Oral Solid Compositions

This Example illustrates an oral solid composition in the form of a capsule (LICAP®) with a liquid composition as fill material containing from about 1% to about 20% of water, wherein said liquid fill material has a pH of about 3 to 6.5 and is substantially stable at room temperature for normal warehouse storage conditions, stable at 104° F. (40° C.) for shipping in hot weather trucks and/or overseas containers, and stable at 39° F. (4° C.) in coolers so that it can be stored under refrigeration conditions.

Preferably, the composition comprises a suitable lipophilic solvent or vehicle, a hydrophilic non-aqueous vehicle, from about 1% to about 20% of water, a preservative, a physical stabilizing ingredient, one or more surfactants, and/or one or more buffer salts that can render the composition pH stable. The composition may also contain nucleotides, oligonucleotides, the monophosphates, diphosphates, triphosphates and cyclic derivatives of these nucleotides, amino acids, vitamins and vitamin-like isoprenoids, peptides and one or more additional components selected from: lipids, medium and short chain triglycerides, starches, polyols, carbohydrates, minerals, electrolytes, amino trace elements, colorings, and anti-oxidants.

Illustrated below are specifically exemplified embodiments of fill material compositions for capsule.

| Formulation I | |
|---|---|
| INGREDIENTS | % w/w |
| Creatyl-L-Glutamine or Creatyl-L-Leucine | 2.10 |
| Medium chain triglyceride | 15.0 |
| Peptides | 3.00 |
| AMP | 12.50 |
| UTP | 0.10 |
| Ubiquinone | 3.30 |
| Oleic Acid | 52.0 |
| Purified Water | 1.0-10.0 |

| Formulation II | |
|---|---|
| INGREDIENTS | % w/w |
| Creatyl-L-Glutamine or Creatyl-L-Leucine | 2.10 |
| Peptides | 3.00 |
| AMP | 12.50 |
| UTP | 0.10 |
| Ubiquinone | 3.30 |
| Polysorbate 80 | 25.0 |
| PEG-40 Hydrogenated Castor Oil | 38.00 |
| PEG esters and monoglycerides | 15.0 |
| Purified Water | QS to 100 |

| Formulation III | |
|---|---|
| INGREDIENTS | % w/w |
| Creatyl-L-Glutamine or Creatyl-L-Leucine | 2.10 |
| Peptides | 3.00 |
| AMP | 12.50 |
| UTP | 0.10 |
| Ubiquinone | 3.30 |
| PEG-400 | 45.0 |
| PEG esters and monoglycerides | 9.00 |
| Polysorbate 80 | 20.0 |
| Buffer Salt(s) | QS to adjust pH |
| Purified Water | QS to 100 |

EXAMPLE 4

Oral Liquid Compositions

This Example illustrates an oral liquid composition containing from 1 gram to 100 grams of protein and from 1 gram to 100 g of carbohydrates per serving. The composition comprises creatyl-amide species, such as creatyl-L-glutamine or creatyl-L-leucine, and is substantially stable at room temperature for normal warehouse storage conditions, stable at 104° F. (40° C.) for shipping in hot weather trucks and/or overseas containers, and stable at 39° F. (4° C.) in coolers so that it can be stored under refrigeration conditions.

Preferably, the composition comprises acid stable protein isolates, or a combination or blend of protein isolates, concentrates and hydrolyzates and caseins in micellar forms, a suitable aqueous solvent or vehicle, a non-aqueous vehicle, a preservative, a physical stabilizing ingredient, one or more surfactants, and/or one or more buffer salts that can render the composition pH stable. The composition may also contain nucleotides, oligonucleotides, the monophosphates, diphosphates, triphosphates and cyclic derivatives of these nucleotides, amino acids, vitamins and vitamin-like isoprenoids, peptides and one or more additional components selected from: lipids, starches, carbohydrates, polyols, minerals, electrolytes, amino trace elements, colorings, flavors, artificial sweeteners, and anti-oxidants.

Illustrated below are specifically exemplified embodiments of protein blend formulations.

| Medium Range pH RTD Protein Blend Formulations | | |
|---|---|---|
| INGREDIENTS | % w/w | Per 16 oz Serving |
| Creatyl-L-Glutamine or Creatyl-L-Leucine | 1.00 | 2.10 |
| Whey Protein Isolate | 6.000 | 30.00 |
| Whey Protein Concentrate | 0.640 | 3.20 |
| Whey Hydrolysate | 0.320 | 1.60 |
| Micellar casein | 0.320 | 1.60 |
| Casein Protein Hydrolysate | 0.000 | 0.00 |
| Potassium Chloride | 0.076 | 0.38 |
| Ascorbic Acid | 0.012 | 0.06 |
| Vitamin E TPGS | 0.052 | 0.26 |
| Riboflavin 100 | 0.000 | 0.00000010 |
| Niacin | 0.000 | 0.0020 |
| Pyrodoxine HCl | 0.000 | 0.000007 |
| Calcium Panthothenate | 0.000 | 0.0011 |
| Magnesium Maleate | 0.020 | 0.1000 |
| d-ribose | 0.040 | 0.2000 |
| Centromix E | 0.600 | 3.00 |
| Saflower Oil | 1.200 | 6.00 |
| Sunflower Oil | 1.200 | 6.00 |
| Medium Chain Triglycerides | 0.800 | 4.00 |
| L-Glutamine | 0.025 | 0.13 |
| Glucose Polymers (Rice trin) | 0.800 | 4.00 |
| Waxy Maize Starch | 1.000 | 5.00 |
| High Amylose Starch (Amylose ADP11P) | 0.100 | 0.50 |
| Magnesium Citrate | 0.124 | 0.62 |
| Microcrystalline Cellulose | 0.100 | 0.50 |
| Malic Acid | 0.140 | 0.70 |
| Citric acid to pH 6.5 | 0.566 | 2.83 |
| Sodium Citrate to pH 6.5 | 0.140 | 0.70 |
| Sucralose | 0.011 | 0.06 |
| Glycerin | 3.000 | 15.00 |
| Na 2 EDTA | 0.050 | 0.25 |
| Sodium Benzoate | 0.090 | 0.45 |
| Potassium Sorbate | 0.190 | 0.95 |
| Water | QS | QS |

| Low pH RTD Protein Formulations | | |
|---|---|---|
| INGREDIENTS | Per 16 oz serving | % w/w |
| Creatyl-L-Glutamine or Creatyl-L-Leucine | 2.10 | 0.25 |
| Whey Protein Isolate Acid Stable | 44.44 | 9.26 |
| Sucralose | 0.12 | 0.025 |

-continued

| Low pH RTD Protein Formulations | | |
|---|---|---|
| INGREDIENTS | Per 16 oz serving | % w/w |
| Na EDTA | 0.24 | 0.050 |
| Potassium Sorbate | 0.96 | 0.200 |
| Sodium Benzoate | 0.48 | 0.100 |
| Citric Acid to pH 3.0 | QS | QS |
| Malic Acid to pH 3.0 | QS | QS |
| Water | 433.8 | 90.37 |
| | 480 | 100 |
| Creatyl-L-Glutamine or Creatyl-L-Leucine | 2.10 | 0.25 |
| Whey Protein Isolate Acid Stable | 44.44 | 9.26 |
| Sucralose | 0.12 | 0.025 |
| Waxy Maize Starch | 4.80 | 1.00 |
| Glucose Polymers (Rice trin) | 0.96 | 0.20 |
| Na EDTA | 0.24 | 0.050 |
| Potassium Sorbate | 0.96 | 0.200 |
| Sodium Benzoate | 0.48 | 0.100 |
| Citric Acid to pH 3.0 | QS | QS |
| Malic Acid to pH 3.0 | QS | QS |
| Water | QS | QS |
| TOTAL | 480 | 100 |

EXAMPLE 5

Aqueous Injectable Compositions

This Example illustrates an aqueous injectable composition suitable for human administration, wherein said composition is isotonic and sterile in nature. The composition comprises creatyl-amide species, such as creatyl-L-glutamine or creatyl-L-leucine, and wherein said injectable preparation has a pH of about 3, and is substantially stable at room temperature for normal warehouse storage conditions, stable at 104° F. (40° C.) for shipping in hot weather trucks and/or overseas containers, and stable at 39° F. (4° C.) in coolers so that it can be stored under refrigeration conditions.

Preferably, the composition comprises a suitable aqueous solvent, a preservative, a physical stabilizing ingredient and/or one or more buffer salts that can render the composition pH stable. The composition may also contain nucleotides, oligonucleotides, the monophosphates, diphosphates, triphosphates and cyclic derivatives of these nucleotides, amino acids, peptides, proteins and carbohydrates.

Illustrated below are specifically exemplified embodiments of aqueous injectable formulations.

| Formulation I | |
|---|---|
| INGREDIENTS | % w/v |
| Creatyl-L-Glutamine or Creatyl-L-Leucine | 1.00 |
| AMP | 12.5 |
| UTP | 0.10 |
| Amino Acids | 3.0-7.0 |
| Polysorbate 80 | 0.40 |
| Sodium CMC | 0.50 |
| Sodium Chloride | 0.90 |
| Benzyl alcohol | 0.90 |
| Buffer Salt(s) | QS to adjust to pH 3-6.5 |
| Sodium Hydroxide | QS to adjust to pH 3-6.5 |
| Water for Injection | QS to 100 |

| Formulation II | |
|---|---|
| INGREDIENTS | % w/v |
| Creatyl-L-Glutamine or Creatyl-L-Leucine | 1.00 |
| AMP | 12.50 |
| UTP | 0.10 |
| Amino Acids | 3.0-7.0 |
| Polysorbate 80 | 0.40 |
| Sorbitol | 40.00 |
| Sodium Chloride | 0.90 |
| Benzyl alcohol | 0.90 |
| Buffer Sat(s) | QS to adjust to pH 3-6.5 |
| Sodium Hydroxide | QS to adjust to pH 3-6.5 |
| Water for Injection | QS to 100 |

| Formulation III | |
|---|---|
| INGREDIENTS | % w/v |
| Creatyl-L-Glutamine or Creatyl-L-Leucine | 2.10 |
| Polysorbate 80 | 0.40 |
| AMP | 12.50 |
| UTP | 0.10 |
| Amino Acids | 3.0-7.0 |
| Sodium Citrate | 0.50 |
| Sodium Chloride | 0.90 |
| Benzyl alcohol | 0.90 |
| Buffer Salt(s) | QS to adjust to pH 3-6.5 |
| Sodium Hydroxide | QS to adjust to pH 3-6.5 |
| Water for Injection | QS to 100 |

EXAMPLE 6

Emulsion Injectable Compositions

This Example illustrates an emulsion injectable composition suitable for human administration, wherein said composition is isotonic and sterile in nature. The composition comprises creatyl-amide species, such as creatyl-L-glutamine or creatyl-L-leucine, and wherein said injectable preparation has a pH of about 3, and is substantially stable at room temperature for normal warehouse storage conditions, stable at 104° F. (40° C.) for shipping in hot weather trucks and/or overseas containers, and stable at 39° F. (4° C.) in coolers so that it can be stored under refrigeration conditions.

Preferably, the composition comprises a suitable aqueous solvent, pharmaceutically acceptable oil (sesame, olive, castor, peanut, cotton seed, etc.), a natural emulsifier such as lecithin or any other synthetic emulsifier being of the polysorbate or ethoxylated glyceride type, a preservative, a physical stabilizing ingredient and/or one or more buffer salts that can render the composition pH stable. The composition may also contain nucleotides, oligonucleotides, the monophosphates, diphosphates, triphosphates and cyclic derivatives of these nucleotides, amino acids, peptides, proteins and carbohydrates.

Illustrated below are specifically exemplified embodiments of emulsion injectable formulations.

| Formulation I | |
|---|---|
| INGREDIENTS | % w/v |
| Creatyl-L-Glutamine or Creatyl-L-Leucine | 1.00 |
| AMP | 12.5 |
| UTP | 0.10 |
| Amino Acids | 3.0-7.0 |
| Sesame Oil | 2.0-12.0 |
| Polysorbate 80 | 0.40 |
| Sodium Chloride | 0.90 |
| Benzyl alcohol | 0.90 |
| Buffer Salt(s) | QS to adjust to pH 3-6.5 |
| Sodium Hydroxide | QS to adjust to pH 3-6.5 |
| Water for Injection | QS to 100 |

| Formulation II | |
|---|---|
| INGREDIENTS | % w/v |
| Creatyl-L-Glutamine or Creatyl-L-Leucine | 1.00 |
| AMP | 12.50 |
| UTP | 0.10 |
| Amino Acids | 3.0-7.0 |
| Olive Oil | 1.0-15.0 |
| Lecithin | 0.50-5.0 |
| Sorbitol | 30.00 |
| Sodium Chloride | 0.90 |
| Benzyl alcohol | 0.90 |
| Buffer Sat(s) | QS to adjust to pH 3-6.5 |
| Sodium Hydroxide | QS to adjust to pH 3-6.5 |
| Water for Injection | QS to 100 |

| Formulation III | |
|---|---|
| INGREDIENTS | % w/v |
| Creatyl-L-Glutamine or Creatyl-L-Leucine | 1.00 |
| Peanut Oil | 1.0-15.0 |
| Polysorbate 80 | 0.2-10.0 |
| AMP | 12.50 |
| UTP | 0.10 |
| Amino Acids | 3.0-7.0 |
| Sodium Citrate | 0.50 |
| Sodium Chloride | 0.90 |
| Benzyl alcohol | 0.90 |
| Buffer Salt(s) | QS to adjust to pH 3-6.5 |
| Sodium Hydroxide | QS to adjust to pH 3-6.5 |
| Water for Injection | QS to 100 |

EXAMPLE 7

Gel Topical Compositions for Skin Application

This Example illustrates a gel topical composition for skin application in humans and animals, wherein said composition is clear or slightly opaque and has a gel consistency so that it can be spread on skin surface. The composition comprises creatyl-amide species, such as creatyl-L-glutamine or creatyl-L-leucine, has a pH of about 3 to 6.5, and is substantially stable at room temperature for normal warehouse storage conditions, stable at 104° F. (40° C.) for shipping in hot weather trucks and/or overseas containers, and stable at 39° F. (4° C.) in coolers so that it can be stored under refrigeration conditions.

Preferably, the composition comprises a suitable aqueous solvent, a preservative, a polymer for imparting consistency, a physical stabilizing ingredient and/or one or more buffer salts that can render the composition pH stable. The composition may also contain nucleotides, oligonucleotides, the monophosphates, diphosphates, triphosphates and cyclic derivatives of these nucleotides, amino acids, vitamins and vitamin-like isoprenoids, peptides, proteins and carbohydrates.

Illustrated below are specifically exemplified embodiments of gel formulations.

| Formulation I | |
|---|---|
| INGREDIENTS | % w/w |
| Creatyl-L-Glutamine or Creatyl-L-Leucine | 1.00 |
| Peptides/Polypeptides | 3.00 |
| AMP | 12.50 |
| UTP | 0.10 |
| Ubiquinone | 3.20 |
| Propylene Glycol | 12.0 |
| Carbomer | 1.00 |
| Buffer Salt(s) | QS to pH 3.0-6.5 |
| Methylparaben | 0.20 |
| Propylparaben | 0.10 |
| Purified Water | QS to 100 |

| Formulation II | |
|---|---|
| INGREDIENTS | % w/w |
| Creatyl-L-Glutamine or Creatyl-L-Leucine | 1.00 |
| Peptides/Polypepetides | 3.00 |
| AMP | 12.50 |
| UTP | 0.10 |
| Ubiquinone | 3.20 |
| Glycerin | 5.00 |
| Hydroxyethylcellulose | 2.00 |
| Triethanolamine | QS to pH 3.0-6.5 |
| Methylparaben | 0.20 |
| Propylparaben | 0.10 |
| Purified Water | QS to 100 |

| Formulation III | |
|---|---|
| INGREDIENTS | % w/w |
| Creatyl-L-Glutamine or Creatyl-L-Leucine | 1.00 |
| Peptides/Polypepetides | 3.00 |
| AMP | 12.50 |
| UTP | 0.10 |
| Ubiquinone | 3.20 |
| Glycerin | 15.0 |
| Poloxamers 407/188 | 10.00 |
| Triethanolamine | QS to pH 3.0-6.5 |
| Methylparaben | 0.025 |
| Propylparaben | 0.015 |
| Purified Water | QS to 100 |

EXAMPLE 8

Cream Topical Compositions for Skin Application

This Example illustrates a cream topical composition for skin application in humans and animals, wherein said composition is an emulsion system or an opacified gel system, and has a creamy consistency so that it can be spread on skin surface. The composition comprises creatyl-amide species, such as creatyl-L-glutamine or creatyl-L-leucine, has a pH of about 3 to 6.5, and is substantially stable at room temperature for normal warehouse storage conditions, stable at 104° F. (40° C.) for shipping in hot weather trucks and/or overseas containers, and stable at 39° F. (4° C.) in coolers so that it can be stored under refrigeration conditions.

Preferably, the composition comprises a suitable aqueous solvent, a preservative, a physical stabilizing ingredient, a surfactant, moisturizers, and/or one or more buffer salts that can render the composition pH stable. The composition may also contain nucleotides, oligonucleotides, the monophosphates, diphosphates, triphosphates and cyclic derivatives of these nucleotides, amino acids, vitamins and vitamin-like isoprenoids, peptides, proteins and carbohydrates.

Illustrated below are specifically exemplified embodiments of cream formulations.

Formulation I

| INGREDIENTS | % w/w |
| --- | --- |
| Creatyl-L-Glutamine or Creatyl-L-Leucine | 1.00 |
| White Petrolatum | 20.0 |
| Stearyl Alcohol | 20.0 |
| Propylene Glycol | 12.0 |
| Peptides/Polypeptides | 3.00 |
| AMP | 12.50 |
| UTP | 0.10 |
| Ubiquinone | 3.20 |
| Sodium lauryl sulfate | 1.00 |
| Methylparaben | 0.20 |
| Propylparaben | 0.10 |
| Buffer Salt(s) | QS to pH 3.0-6.5 |
| Purified Water | QS to 100 |

Formulation II

| INGREDIENTS | % w/w |
| --- | --- |
| Creatyl-L-Glutamine or Creatyl-L-Leucine | 1.00 |
| Peptides/Polypeptides | 3.00 |
| AMP | 12.50 |
| UTP | 0.10 |
| Ubiquinone | 3.20 |
| Mineral Oil | 15.0 |
| Lanolin Alcohol | 10.0 |
| Cetyl Alcohol | 0.20 |
| Beeswax | 4.00 |
| Sorbitan Monoleate | 5.00 |
| Glycerin | 5.00 |
| Borax | 0.30 |
| Triethanolamine | 0.70 |
| Methylparaben | 0.20 |
| Propylparaben | 0.10 |
| Buffer Salt(s) | QS to pH 3.0-6.5 |
| Purified Water | QS to 100 |

Formulation III

| INGREDIENTS | % w/w |
| --- | --- |
| Creatyl-L-Glutamine or Creatyl-L-Leucine | 1.00 |
| Peptides/Polypeptides | 3.00 |
| AMP | 12.50 |
| UTP | 0.10 |
| Ubiquinone | 3.20 |
| Glyceryl Monostearate | 10.0 |
| Lanolin | 2.00 |
| Glycerin | 10.0 |
| Stearyl Pyridinium Chloride | 1.50 |
| Methylparaben | 0.025 |
| Propylparaben | 0.015 |
| Buffer Salt(s) | QS to pH 3.0-6.5 |
| Purified Water | QS to 100 |

EXAMPLE 9

Deep-Penetrating Transdermal Compositions

This Example illustrates a deep-penetrating transdermal composition for application in humans and animals, wherein said composition is a solution, a gel-like or an emulsion-like system or an opacified gel-like system, and has a consistency so that it can be spread on skin surface. The composition comprises creatyl-amide species, such as creatyl-L-glutamine or creatyl-L-leucine, and is substantially stable at room temperature for normal warehouse storage conditions, stable at 104° F. (40° C.) for shipping in hot weather trucks and/or overseas containers, and stable at 39° F. (4° C.) in coolers so that it can be stored under refrigeration conditions.

Preferably, the composition comprises a suitable aqueous solvent, a non-aqueous solvent, one or more penetrating enhancers, a preservative, a physical stabilizing ingredient, one or more surfactants, moisturizers, and/or one or more buffer salts that can render the composition pH stable. The composition may also contain nucleotides, oligonucleotides, the monophosphates, diphosphates, triphosphates and cyclic derivatives of these nucleotides, amino acids, vitamins and vitamin-like isoprenoids, peptides, proteins and carbohydrates.

Illustrated below are specifically exemplified embodiments of transdermal compositions.

Formulation I

| INGREDIENTS | % w/w |
| --- | --- |
| Creatyl-L-Glutamine or Creatyl-L-Leucine | 5.00 |
| N-methylpyrrolidone | 15.0 |
| Peptides | 3.00 |
| AMP | 12.50 |
| UTP | 0.10 |
| Ubiquinone | 3.20 |
| Alcohol USP | 2.00 |
| Benzyl alcohol | 1.00 |
| Buffer Salt(s) | QS to pH 3.0-6.5 |
| Purified Water | QS to 100 |

Formulation II

| INGREDIENTS | % w/w |
| --- | --- |
| Creatyl-L-Glutamine or Creatyl-L-Leucine | 5.00 |
| Peptides | 3.00 |

-continued

| Formulation II | |
|---|---|
| INGREDIENTS | % w/w |
| AMP | 12.50 |
| UTP | 0.10 |
| Ubiquinone | 3.20 |
| Ethoxydiglycol | 25.0 |
| Alcohol USP | 2.00 |
| PEG esters and monoglycerides | 15.0 |
| Benzyl alcohol | 1.00 |
| Buffer Salt(s) | QS to pH 3.0-6.5 |
| Purified Water | QS to 100 |

| Formulation III | |
|---|---|
| INGREDIENTS | % w/w |
| Creatyl-L-Glutamine or Creatyl-L-Leucine | 5.00 |
| Peptides | 3.00 |
| AMP | 12.50 |
| UTP | 0.10 |
| Ubiquinone | 3.20 |
| Propylene Glycol | 25.0 |
| Alcohol USP | 4.00 |
| Polysorbate 80 | 10.0 |
| Benzyl alcohol | 1.00 |
| Buffer Salt(s) | QS to pH 3.0-6.5 |
| Purified Water | QS to 100 |

EXAMPLE 10

Transdermal Patch Delivery Systems

This Example illustrates a transdermal patch delivery system, comprising a liner, an adhesive, a backing and an aqueous liquid reservoir composition. The aqueous liquid reservoir composition is a solution or a suspension, comprising creatyl-amide species, such as creatyl-L-glutamine or creatyl-L-leucine, wherein said transdermal patch is substantially stable at room temperature for normal warehouse storage conditions, stable at 104° F. (40° C.) for shipping in hot weather trucks and/or overseas containers, and stable at 39° F. (4° C.) in coolers so that it can be stored under refrigeration conditions.

Preferably, the composition comprises a suitable aqueous solvent, a non-aqueous solvent, one or more penetrating enhancers, a preservative, a physical stabilizing ingredient, one or more surfactants, and/or one or more buffer salts that can render the composition pH stable. The composition may also contain nucleotides, oligonucleotides, the monophosphates, diphosphates, triphosphates and cyclic derivatives of these nucleotides, amino acids, vitamins and vitamin-like isoprenoids, peptides, proteins and carbohydrates.

Illustrated below are specifically exemplified embodiments of liquid reservoirs for transdermal patch.

| Formulation I | |
|---|---|
| INGREDIENTS | % w/w |
| Creatyl-L-Glutamine or Creatyl-L-Leucine | 5.00 |
| N-methylpyrrolidone | 10.0 |
| Peptides | 3.00 |
| AMP | 12.50 |

-continued

| Formulation I | |
|---|---|
| INGREDIENTS | % w/w |
| UTP | 0.10 |
| Ubiquinone | 3.20 |
| Alcohol USP | 45.0 |
| Benzyl alcohol | 1.00 |
| Buffer Salt(s) | QS to pH 3.0-6.5 |
| Purified Water | QS to 100 |

| Formulation II | |
|---|---|
| INGREDIENTS | % w/w |
| Creatyl-L-Glutamine or Creatyl-L-Leucine | 5.00 |
| Peptides | 3.00 |
| AMP | 12.50 |
| UTP | 0.10 |
| Ubiquinone | 3.20 |
| Ethoxydiglycol | 20.0 |
| Alcohol USP | 50.0 |
| Benzyl alcohol | 1.00 |
| Buffer Salt(s) | QS to pH 3.0-6.5 |
| Purified Water | QS to 100 |

| Formulation III | |
|---|---|
| INGREDIENTS | % w/w |
| Creatyl-L-Glutamine or Creatyl-L-Leucine | 5.00 |
| Peptides | 3.00 |
| AMP | 12.50 |
| UTP | 0.10 |
| Ubiquinone | 3.20 |
| Propylene Glycol | 20.0 |
| Alcohol USP | 40.0 |
| Polysorbate 80 | 5.0 |
| Benzyl alcohol | 1.00 |
| Buffer Salt(s) | QS to pH 3.0-6.5 |
| Purified Water | QS to 100 |

EXAMPLE 11

Stability of Creatyl-Amide Compositions

This Example demonstrates that amide protected bioactive creatine compositions of the subject invention are stable at room temperature, refrigeration temperature and elevated temperature. Specifically exemplified herein are three different formulations prepared using stable creatyl-L-glutamine (C-L-G) at a concentration of 1.00 mg/ml between pH 3.0 to 7.0. These formulations are described below.

| Formulation I | |
|---|---|
| INGREDIENTS Formulation pH 3.33 | % w/w |
| Purified water | 97.1 |
| Creatyl-L-Glutamine | 1 |
| Gamma Butyrobetaine | 0.0156 |
| Glycerin | 1.067 |
| Anserine | 0.052 |
| Caffeine | 0.06 |

-continued

| Formulation I | |
|---|---|
| INGREDIENTS Formulation pH 3.33 | % w/w |
| Magnesium Tanshinoate | 0.0000009 |
| L-Leucine | 0.104 |
| L-Isoleucine | 0.052 |
| L-Valine | 0.0208 |
| 1,3-di-n-propyl-7-propargylxanthine | 1E-10 |
| Geranamine | 0.0004 |
| Citric acid to pH 3.33 | 0.179 |
| Sodium benzoate | 0.052 |
| Potassium sorbate | 0.01 |
| Bis picolinate vanadium | 0.0000002 |
| Salt | 0.005 |
| Potassium phosphate dibasic | 0.0206 |
| Sodium Erythorbate | 0.000001 |
| Nisaplin | 0.000001 |
| Sucralose | 0.073 |
| Malic acid | 0.083 |
| Flavor Melon | 0.105 |

| Formulation II | |
|---|---|
| INGREDIENTS Formulation pH 7-8 | % w/w |
| Purified water | 99.0 |
| Creatyl-L-Glutamine | 1.0 |

| Formulation III | |
|---|---|
| INGREDIENTS Formulation pH 3.33 | % w/w |
| Purified water | 97.1 |
| Creatyl-L-Glutamine | 1 |
| Citric acid to pH 3.33 | 0.179 |
| Sodium benzoate | 0.052 |
| Potassium sorbate | 0.01 |
| Potassium phosphate dibasic | 0.0206 |
| Sucralose | 0.073 |
| Malic acid | 0.083 |
| Flavor Melon | 0.105 |

The above described formulations were stored in glass vials at room temperature (25° C., 77° F.), at refrigerator temperature (4° C., 39° F.) and at elevated temperature (40° C., 104° F.) in vials. These samples were assayed by HPLC at periodic intervals for minimum of 60 days for creatyl-L-glutamine (C-L-G) and creatinine (degradation product of creatine) content. The % recovery results are presented below.

| Ready To Drink Formulation (pH = 3.3) | | | | | | |
|---|---|---|---|---|---|---|
| | Room Temperature | | 4° C. (39° F.) | | 40° C. (104° F.) | |
| | C-L-G | Creatinine | C-L-G | Creatinine | C-L-G | Creatinine |
| Initial | 98.81 | 1.19 | N/A | N/A | N/A | N/A |
| 1 Day | 99.16 | 0.84 | 99.23 | 0.77 | 98.92 | 1.08 |
| 3 Days | 98.76 | 1.24 | 98.96 | 1.04 | 97.96 | 2.04 |
| 1 Week | 98.91 | 1.09 | 99.28 | 0.72 | 97.05 | 2.95 |
| 2 Weeks | 98.59 | 1.41 | 99.27 | 0.73 | 95.45 | 4.55 |
| 3 Weeks | 98.33 | 1.67 | 99.16 | 0.84 | 94.49 | 5.51 |
| 4 Weeks | 97.95 | 2.05 | 98.98 | 1.02 | 93.25 | 6.75 |
| 6 Weeks | 97.41 | 2.59 | 98.22 | 1.78 | 89.12 | 10.88 |
| 2 Months | 97.45 | 2.55 | 98.88 | 1.12 | 87.46 | 11.50 |
| 3 Months | 94.32 | 5.68 | 94.67 | 5.33 | 89.83 | 10.17 |

| Neutral Formulation (pH = 7.0-8.0) | | | | | | |
|---|---|---|---|---|---|---|
| | Room Temperature | | 4° C. (39° F.) | | 40° C. (104° F.) | |
| | C-L-G | Creatinine | C-L-G | Creatinine | C-L-G | Creatinine |
| Initial | 99.15 | 0.85 | N/A | N/A | N/A | N/A |
| 1 Day | 99.15 | 0.85 | 99.20 | 0.80 | 98.77 | 1.23 |
| 3 Days | 98.41 | 1.59 | 99.11 | 0.89 | 89.95 | 10.05 |
| 1 Week | 93.53 | 6.47 | 99.09 | 0.91 | 91.03 | 8.97 |
| 2 Weeks | 74.62 | 25.38 | 99.03 | 0.97 | 27.12 | 72.88 |
| 3 Weeks | 52.89 | 47.11 | 98.95 | 1.05 | 36.96 | 63.04 |
| 4 Weeks | 39.47 | 60.53 | 99.00 | 1.00 | 16.15 | 83.85 |
| 6 Weeks | 5.47 | 94.53 | 97.29 | 2.71 | 0.00 | 100.00 |
| 2 Months | 0.00 | 100.00 | 97.90 | 2.10 | 0.00 | 100.00 |
| 3 Months | 0.00 | 100.00 | 97.77 | 2.23 | 0.00 | 100.0 |

| Acidic Formulation (pH = 3.3) | | | | | | |
|---|---|---|---|---|---|---|
| | Room Temperature | | 4° C. (39° F.) | | 40° C. (104° F.) | |
| | C-L-G | Creatinine | C-L-G | Creatinine | C-L-G | Creatinine |
| Initial | 99.23 | 0.77 | N/A | N/A | N/A | N/A |
| 1 Day | 99.17 | 0.83 | 99.23 | 0.77 | 98.89 | 1.11 |
| 3 Days | 99.03 | 0.97 | 93.52 | 0.74 | 98.21 | 1.79 |
| 1 Week | 98.91 | 1.09 | 99.30 | 0.70 | 97.31 | 2.69 |
| 2 Weeks | 98.91 | 1.09 | 99.29 | 0.71 | 95.87 | 3.62 |
| 3 Weeks | 98.47 | 1.53 | 99.19 | 0.81 | 94.94 | 5.06 |
| 4 Weeks | 98.12 | 1.88 | 98.97 | 1.03 | 93.71 | 6.29 |
| 6 Weeks | 96.42 | 3.58 | 98.32 | 1.68 | 89.69 | 10.31 |
| 2 Months | 96.76 | 3.24 | 98.50 | 1.50 | 89.05 | 10.95 |
| 3 Months | 95.63 | 4.37 | 96.365 | 3.65 | 88.90 | 11.10 |

The results show that creatyl-L-glutamine (C-L-G) aqueous solutions of the subject invention remain stable for more than 90 days at room temperature (25° C., 77° F.) and refrigerator temperature (4° C., 39° F.), and thus are suitable for normal warehouse storage conditions and also refrigeration conditions. The C-L-G composition is also stable for more than 30 days at elevated temperature (40° C., 104° F.), which is suitable for shipping in hot weather trucks and/or overseas containers.

EXAMPLE 12

Conversion of Creatine to Creatinine

The following tables illustrate the rate of conversion to creatinine from creatine monohydrate and disodium creatine phosphate tetrahydrate solutions.

| Preparation: Creatine Monohydrate Aqueous Solution Concentration: 0.250 mg/mL pH: 7.0 Condition: 40 C.° | | | |
|---|---|---|---|
| | Time | | |
| Test | INITIAL | 3 day | 31 Days |
| COP Assay | 0.257 mg/mL | 0.242 mg/ml | 0.251 mg/mL |
| Creatinine | 0.000 mg/mL | 0.008 mg/mL | 0.068 mg/mL |
| pH | 7.0 | | |

| Preparation: Creatine Monohydrate Aqueous Solution Concentration: 0.250 mg/mL | | | | | |
|---|---|---|---|---|---|
| | Time | | | | |
| Test | INITIAL | 3 day | 10 days | 21 days | 39 Days |
| | pH: 3.0 Condition: 40 C.° | | | | |
| COP Assay | 0.245 mg/mL | 0.091 mg/ml | 0.036 mg/mL | 0.029 mg/mL | 0.030 mg/mL |
| Creatinine | 0.000 mg/mL | 0.125 mg/mL | 0.177 mg/ml | 0.186 mg/mL | 0.186 mg/mL |
| pH | 3.0 | | | | |
| | pH: 3.0 Condition: 25 C.° | | | | |
| COP Assay | 0.245 mg/mL | 0.219 mg/ml | 0.214 mg/mL | 0.151 mg/mL | 0.072 mg/mL |
| Creatinine | 0.000 mg/mL | 0.026 mg/mL | 0.072 mg/ml | 0.111 mg/mL | 0.154 mg/mL |
| pH | 3.0 | | | | |

| Preparation: Disodium Creatine Phosphate Tetrahydrate Aqueous Solution Concentration: 0.250 mg/mL | | | | | |
|---|---|---|---|---|---|
| | Time | | | | |
| Test | INITIAL | 3 day | 10 days | 21 days | 39 Days |
| | pH: 7.0 Condition: 40 C.° | | | | |
| COP Assay | 0.247 mg/mL | 0.166 mg/ml | 0.066 mg/mL | 0.015 mg/mL | 0.002 mg/mL |
| Creatine Monohydrate | 0.00 mg/mL | 0.042 mg/mL | 0.114 mg/mL | 0.122 mg/mL | 0.108 mg/mL |
| Creatinine | 0.000 mg/mL | 0.004 mg/mL | 0.012 mg/mL | 0.020 mg/ml | 0.030 mg/mL |
| pH | 7.0 | | | | |
| | pH: 7.0 Condition: 25 C.° | | | | |
| COP Assay | 0.247 mg/mL | 0.229 mg/ml | 0.231 mg/mL | 0.182 mg/mL | 0.141 mg/mL |
| Creatine Monohydrate | 0.00 mg/mL | 0.0.14 mg/mL | 0.041 mg/mL | 0.069 mg/mL | 0.089 mg/mL |
| Creatinine | 0.000 mg/mL | 0.000 mg/mL | 0.000 mg/mL | 0.000 mg/ml | 0.000 mg/mL |
| pH | 7.0 | | | | |

| 1. Preparation: Disodium Creatine Phosphate Tetrahydrate Aqueous Solution Concentration: 0.250 mg/mL | | | | | |
|---|---|---|---|---|---|
| | Time | | | | |
| Test | INITIAL | 3 day | 10 days | 21 days | 39 Days |
| | pH: 3.0 Condition: 40 C.° | | | | |
| COP Assay | 0.247 mg/mL | 0.000 mg/ml | 0.000 mg/mL | 0.000 mg/mL | 0.000 mg/ml |
| Creatine Monohydrate | 0.004 mg/mL | 0.042 mg/mL | 0.017 mg/mL | 0.011 mg/mL | 0.012 mg/ml |
| Creatinine | 0.000 mg/mL | 0.054 mg/mL | 0.086 mg/mL | 0.080 mg/ml | 0.081 mg/mL |

-continued

1. Preparation: Disodium Creatine Phosphate Tetrahydrate Aqueous Solution
Concentration: 0.250 mg/mL

| Test | INITIAL | 3 day | 10 days | 21 days | 39 Days |
|---|---|---|---|---|---|
| pH | 3.0 | | | | |
| | | pH: 3.0 Condition: 25 C.° | | | |
| COP Assay | 0.247 mg/mL | 0.000 mg/ml | 0.000 mg/mL | 0.000 mg/mL | 0.00 mg/ml |
| Creatine Monohydrate | 0.000 mg/ml | 0.095 mg/mL | 0.092 mg/mL | 0.065 mg/mL | 0.031 mg/mL |
| Creatinine | 0.000 mg/mL | 0.014 mg/mL | 0.034 mg/mL | 0.050 mg/ml | 0.069 mg/mL |
| pH | 3.0 | | | | |

REFERENCES

1. Rawson E S, Volek J S. Effects of creatine supplementation and resistance training on muscle strength and weightlifting performance. J Strength Cond Res 2003; 17:822-31.
2. Powers M E, Arnold B L, Weltman A L, et al. Creatine Supplementation Increases Total Body Water Without Altering Fluid Distribution. J Athl Train 2003; 38:44-50.
3. Wyss M, Schulze A. Health implications of creatine: can oral creatine supplementation protect against neurological and atherosclerotic disease? Neuroscience 2002; 112:243-60.
4. Stout J R, Eckerson J M, May E, Coulter C, Bradley-Popovich G E. Effects of resistance exercise and creatine supplementation on myasthenia gravis: a case study. Med Sci Sports Exerc 2001; 33:869-72.
5. Vorgerd M, Grehl T, Jager M, et al. Creatine therapy in myophosphorylase deficiency (McArdle disease): a placebo-controlled crossover trial. Arch Neurol 2000; 57:956-63.
6. Harris R C, Nevill M, Harris D B, Fallowfield J L, Bogdanis G C, Wise JA. Absorption of creatine supplied as a drink, in meat or in solid form. J Sports Sci 2002; 20:147-51.
7. Hass C J, Collins M A, Juncos J L. Resistance training with creatine monohydrate improves upper-body strength in patients with Parkinson disease: a randomized trial. Neurorehabil Neural Repair 2007; 21:107-15.
8. Poortmans J R, Francaux M. Adverse effects of creatine supplementation: fact or fiction? Sports Med 2000; 30:155-70.
9. Kreider R B, Melton C, Rasmussen C J, et al. Long-term creatine supplementation does not significantly affect clinical markers of health in athletes. Mol Cell Biochem 2003; 244:95-104.
10. Buford T W, Kreider R B, Stout J R, et al. International Society of Sports Nutrition position stand: creatine supplementation and exercise. J Int Soc Sports Nutr 2007; 4:6.
11. Juhasz I, Gyore I, Csende Z, Racz L, Tihanyi J. Creatine supplementation improves the anaerobic performance of elite junior fin swimmers. Acta Physiol Hung 2009; 96:325-36.
12. Athanasios E, Konstantina V, Paraskevi K, Nikolaos N. Clinical Applications of Creatine Supplementation on Paediatrics. Curr Pharm Biotechnol 2009.
13. Ling J, Kritikos M, Tiplady B. Cognitive effects of creatine ethyl ester supplementation. Behav Pharmacol 2009.
14. Spillane M, Schoch R, Cooke M, et al. The effects of creatine ethyl ester supplementation combined with heavy resistance training on body composition, muscle performance, and serum and muscle creatine levels. J Int Soc Sports Nutr 2009; 6:6.

What is claimed is:

1. An aqueous composition for administering, to a mammal, an amide-protected, biologically active form of creatine that is stable in an aqueous system, wherein said composition comprises:
    a) at least one creatyl-amide species, and
    b) water;
    wherein, in said creatyl-amide species, the carboxylic acid group of creatine is linked, via an amide bond, to an amino group of a species selected from the group consisting of glutamine, leucine, arginine, histidine, isoleucine, lysine, methionine, threonine, tryptophan, tyrosine, valine, alanine, asparagine, aspartate, cysteine, glutamate, glycine, proline, serine, carnosine, 1-methylhistidine, beta-alanyl-1-methylhistidine sarcosine, β-alanine, citrulline, ornithine, prolinamide, 5-hydroxylysine, alanyl-L-glutamine, taurine, and geranamine.

2. The composition, according to claim 1, wherein the creatyl-amide species is:
creatyl-L-glutamine

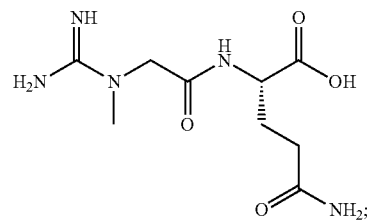 [SMILES: CN(CC(=O)N[C@@H](CCC(N)=O)C(=O)O)C(=N)N]

or
creatyl-L-leucine

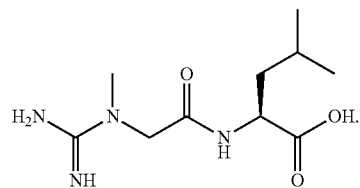 [SMILES: CC(C)C[C@H](NC(=O)CN(C)C(=N)N)C(=O)O]

3. The composition, according to claim 1, wherein the creatyl-amide species is: creatyl-L-carnosine, creatyl-1-methylhistidine, or creatyl-beta-alanyl-1-methylhistidine.

4. The composition, according to claim 1, having a pH of about 1.5 to about 6.5.

5. The composition, according to claim 1, wherein said at least one creatyl-amide species is present in an amount between about 0.01% and about 10% by weight.

6. The composition, according to claim 1, further comprising one or more ions selected from the group consisting of: sodium, potassium, zinc, calcium, and magnesium.

7. The composition, according to claim 6, wherein said one or more ions is present in an amount between about 0.001% and about 5% by weight.

8. The composition, according to claim 1, further comprising one or more additional materials selected from the group consisting of flavoring agents, colorants, viscosity modifiers, preservatives, fragrances, amino acids and their salts, vitamins, minerals, fatty acids, enzymes, co-enzymes, mono-glycerides, di-glycerides, tri-glyceride ester oils emulsifiers, hydrolyzed proteins, whey protein, stabilizers, flow modifiers, chelating agents, anti-oxidants, anti-microbials, benzoates, alcohols, esters of para-hydroxybenzoic acid, propionates, and surfactants.

9. The composition, according to claim 1, further comprising one or more beverages selected from the group consisting of milk products, soy products, ice cream, yogurt, citrus fruit juices, non-citrus fruit juices, and vegetable juices.

10. The composition, according to claim 1, comprising an anti-microbial preservative present in an effective amount to inhibit microbial growth, wherein the preservative is selected from the group consisting of an ester of para-hydroxy benzoic acid, an ester of propionates, and a sorbate salt.

11. The composition, according to claim 1, in the form of a composition for oral administration, an aqueous injectable formulation, an injectable emulsion composition, a gel formulation, a cream formulation, a transdermal system, a transdermal patch system, a liquid buccal sublingual solution, an oral solid composition, or an oral liquid composition with protein.

12. The composition, according to claim 1, which is a liquid composition.

* * * * *

UNITED STATES PATENT AND TRADEMARK OFFICE
CERTIFICATE OF CORRECTION

| | | |
|---|---|---|
| PATENT NO. | : 8,445,466 B2 | Page 1 of 1 |
| APPLICATION NO. | : 12/756686 | |
| DATED | : May 21, 2013 | |
| INVENTOR(S) | : John H. Owoc et al. | |

It is certified that error appears in the above-identified patent and that said Letters Patent is hereby corrected as shown below:

On the Title Page

Item (76), naming the inventors, --Liangxi Li, Plantation, FL (US)-- should be inserted after "John H. Owoc, Weston, FL (US)."

Signed and Sealed this
Eighth Day of August, 2017

Joseph Matal
*Performing the Functions and Duties of the*
*Under Secretary of Commerce for Intellectual Property and*
*Director of the United States Patent and Trademark Office*

EX PARTE REEXAMINATION CERTIFICATE (12596th)

United States Patent
Owoc et al.

(10) Number: US 8,445,466 C1
(45) Certificate Issued: May 10, 2024

(54) STABLE AQUEOUS COMPOSITIONS COMPRISING AMIDE-PROTECTED BIOACTIVE CREATINE SPECIES AND USES THEREOF

(75) Inventors: John H. Owoc, Weston, FL (US); Liangxi Li, Plantation, FL (US)

(73) Assignee: JHO Intellectual Property Holdings, LLC

Reexamination Request:
No. 90/013,933, Apr. 7, 2017

Reexamination Certificate for:
Patent No.: 8,445,466
Issued: May 21, 2013
Appl. No.: 12/756,686
Filed: Apr. 8, 2010

Certificate of Correction issued Aug. 8, 2017

(51) Int. Cl.
*A61K 31/198* (2006.01)
*A61K 9/00* (2006.01)

(52) U.S. Cl.
CPC .......... *A61K 31/198* (2013.01); *A61K 9/0014* (2013.01); *A61K 9/0019* (2013.01); *A61K 9/006* (2013.01); *A61K 9/0095* (2013.01)

(58) Field of Classification Search
None
See application file for complete search history.

(56) References Cited

To view the complete listing of prior art documents cited during the proceeding for Reexamination Control Number 90/013,933, please refer to the USPTO's Patent Electronic System.

*Primary Examiner* — Alan D Diamond

(57) ABSTRACT

The present invention provides amide-protected creatine molecules and compositions, containing one or more bioactive forms of creatine in aqueous compositions, wherein bioactive forms of creatine do not appreciably degrade into creatinine. Also provided are various beneficial effects of administering aqueous compositions having at least one amide-protected creatine molecule.

At the time of issuance and publication of this certificate, the patent remains subject to pending reissue application number 16/549,396 filed Aug. 23, 2019. The claim content of the patent may be subsequently revised if a reissue patent is issued from the reissue application.

EX PARTE REEXAMINATION CERTIFICATE

THE PATENT IS HEREBY AMENDED AS INDICATED BELOW.

AS A RESULT OF REEXAMINATION, IT HAS BEEN DETERMINED THAT:

Claims 1-12 are cancelled.

* * * * *